United States Patent [19]

Baines et al.

[11] 4,269,823

[45] May 26, 1981

[54] PERIODONTAL DENTAL PREPARATION

[75] Inventors: Eric Baines, Flixton; Kenneth Harvey, Wilmslow, both of England

[73] Assignee: Colgate-Palmolive Co., New York, N.Y.

[21] Appl. No.: 143,068

[22] Filed: Apr. 24, 1980

[30] Foreign Application Priority Data

May 15, 1979 [GB] United Kingdom ............... 16874/79

[51] Int. Cl.³ ............................................. A61K 7/18
[52] U.S. Cl. ........................................ 424/52; 424/57
[58] Field of Search .................................... 424/48–58

[56] References Cited

FOREIGN PATENT DOCUMENTS 2242553 3/1974 Fed. Rep. of Germany .

OTHER PUBLICATIONS

Slovokhotnova, Chem. Abstr. 71, #10826(d), (1969), Role of B-Vitamins in Preventing Dental Caries.

Vogel et al., Chem. Abstr. 86, #657455, (1977), The Effect of Folic Acid on Gingival Health.

Dreizen et al., J. Dent. Res., 49(3):616–620, May, Jun. 1970, The Effect of Folic Acid Deficiency on the Marmoset Oral Mucosa.

Abstr. In Chem. Abstr. 73, #106848e, (1970).

Koehler, Chem. Abstr. 80, #149035z, (1974), of Ger. Off. No. 2,342,553, Mar. 7, 1974.

*Primary Examiner*—Shep K. Rose
*Attorney, Agent, or Firm*—R. L. Stone; M. M. Grill; H. S. Sylvester

[57] ABSTRACT

A periodontal dental preparation is disclosed comprising folic acid, a dentally acceptable water-insoluble polishing agent which reduces the soluble folic acid present in the preparation and a fluorine-containing agent which increases retention of soluble folic acid in said preparation, the fluorine-containing agent comprising an alkali metal fluoride, and alkali metal monofluorophosphate, or a mixture thereof.

7 Claims, No Drawings

PERIODONTAL DENTAL PREPARATION

Folic acid is a well known anti-irritant and anti-inflammatory material. A normal adult requires at least about 0.3 mg. of this material in order to maintain oral health. Folic acid is a conjugate bound to up to seven molecules of glutamic acid. It has the structural formula:

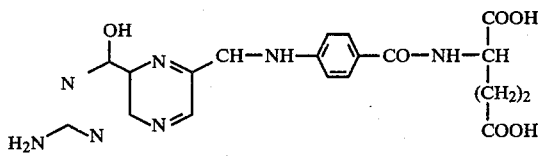

It was reported by R. Vogel et al of New Jersey Dental School, Newark, N.J. in AADR Abstracts 1977, 34 "Effect of Folic Acid Rinse On Gingival Health" and IADR Abstracts 1977, 565 "Folic Acid and Experimentally Produced Gingivitis", that folic acid can be directly absorbed by the gingiva from a rinse solution resulting in a significant reduction in gingival inflammation.

Unfortunately, when a dental preparation is formulated including a dentally acceptable water-insoluble polishing agent the retention of soluble folic acid available to be absorbed in the gingiva can be substantially reduced.

According to the present invention a periodontal dental preparation comprises folic acid, a dentally acceptable water-insoluble polishing agent which reduces the soluble folic acid present in the preparation and a fluorine-containing agent which increases retention of soluble folic acid in the preparation, the fluorine-containing agent comprising an alkali metal fluoride, an alkali metal monofluorophosphate of a mixture thereof.

The periodontal dental preparation comprising folic acid, polishing agent and alkali metal fluoride is typically a dental cream or gel. The initial pH of the preparation may be about 4-10, preferably about 6-9 (on a 20% slurry). Below a pH of about 4, large amounts of folic acid would be removed.

Folic acid is typically present in amount of about 0.01-5% by weight, preferably about 0.05-0.5%.

Various water-insoluble polishing agents which are normally dentally acceptable cause removal of at least a portion of the folic acid from solution in the preparation. For instance, sodium aluminosilicate (e.g. of low alumina content; essentially sodium silicate with a small amount of combined alumina) and insoluble sodium metaphosphate may cause insolubility or remove about 70% or more of the folic acid upon aging for 3 months at room temperature and at 43° C. Lesser, but still meaningful amounts of folic acid (e.g. about 15-25%) may be insolubilized or removed when the polishing material is hydrated alumina (e.g. alpha-alumina trihydrate) or calcium carbonate. Certain polishing agents, such as dicalcium phosphate dihydrate as substantially the sole polishing agent present, are highly compatible with folic acid and do not cause it to be removed. Such polishing materials do not require the presence of an additive to increase retention of soluble folic acid.

The dentally acceptable water-insoluble polishing agent typically comprises about 10-75% by weight of the dental preparation, preferably about 15-55% by weight.

The fluorine-containing agent increases retention of soluble folic acid in the dental preparation. It is also available to provide fluoride to dental material and thereby reduce formation of caries. The alkali metal of the fluorine-containing agent may be lithium, sodium or potassium as well as, for purpose of this disclosure, ammonium. The fluorophosphate compound may be the usual fluorophosphate anion, $PO_3F^{-2}$, or a monofluoropolyphosphate anion, $P_3O_9F^{-4}$.

Sodium fluoride and sodium monofluorophosphate, $Na_2PO_3F$, are preferred. The fluorine-containing agent is present in amount which provides about 0.01-1% by weight fluorine preferably about 0.1% to the dental preparation, e.g., about 0.02-2%, preferably about 0.24% of sodium fluoride and about 0.076-7.6%, preferably about 0.8% of sodium monofluorophosphate.

The dental preparation can be a cream or gel with liquids and solids proportioned to form a creamy or gel mass of desirable consistency. In general, liquids in the preparation comprise chiefly water and humectants such as glycerine, sorbitol, propylene glycol, polythylene glycol (e.g., molecule weight about 600) or the like, including suitable mixtures thereof. It is advantageous usually to use a mixture of both water and a binder or humectant such as glycerine and/or sorbitol. It is preferred to use at least about 20% liquid, preferably for a cream 10.50% water, and about 20-80% humectant and for a gel 0 to about 30% water, 0 to about 80% glycerine and about 20-80% sorbitol.

The solid portion of the vehicle is a gelling agent, such as the natural and synthetic gums and gum-like materials, such as Irish moss, gum tragacanth, alkali metal carboxyethyl cellulose and hydroxyethyl carboxymethyl cellulose, polyvinyl pyrrolidone, starch, xanthan, water-soluble hydrophilic colloidal carboxyvinyl polymers, such as those sold under the trademark Carbopol 934 and 940 and synthetic inorganic silicated clays such as those sold under the trademark Laponite CP and Laponite SP. These grades of Laponite have the formula:

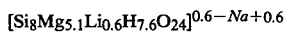

The solid portion of the vehicle is typically present in an amount up to about 10% by weight of the dentifrice and preferably about 0.5-5% by weight. When employed, grades of Laponite are preferably used in amounts of about 1-5% by weight.

Organic surface-active agents may be used in the preparation of the present invention to achieve increased prophylactic action, assist in achieving thorough and complete dispersion of the instant compositions throughout the oral cavity, and render the instant compositions more cosmetically acceptable. The organic surface-active material may be anionic, nonionic, ampholytic or cationic in nature, and it is preferred to employ as the surface-active agent a detersive material which imparts to the composition detersive and foaming properties. Suitable types of such detergents are water-soluble salts of higher fatty acid monoglyceride monosulphates, such as the sodium salt of the monosulphated monoglyceride of hydrogenated coconut oil fatty acids, higher alkyl sulphates, such as sodium lauryl sulphate, alkyl aryl sulphonates, such as sodium dodecyl benzene sulphonate, olefin sulphonates, such as sodium olefin sulphonate in which the olefin group contains 12-21 carbon atoms, higher alkyl sulphoacetates, higher fatty acid ester of 1,2-dihydroxy propane sulphonates, and the substantially saturated higher aliphatic acyl amides of lower aliphatic amino carboxylic acid compounds, such as those having 12 to 16 carbon atoms in the fatty acid, alkyl or acyl radicals and the like. Examples of the last mentioned amides are N-lauroyl sarcosine, and the sodium potassium, and ethanolamine salts of N-lauroyl, N-myristoyl or N-palmitoyl sarcosine, which should be substantially free from soap or similar higher fatty acid material which tends to substantially reduce the effect of these compounds in preparations of the present invention. The amides are particularly advantageous since these materials exhibit a prolonged and marked effect in the inhibition of acid formulation in the oral cavity due to carbohydrates breakdown in addition to exerting some reduction in the solubility of tooth enamel in acid solutions. Another desirable material is a long chain fatty acid sodium monoglyceride sulphonate used alone or in combination with sodium lauryl sulphate.

Other particularly suitable surface-active materials include nonionic agents such as condensates of sorbitan monostearate with approximately 60 moles of ethylene oxide, condensates of propylene glycol ("Pluronics") and amphoteric agents such as quaternized derivatives, which are available under the trademark "Miranol" such as Miranol C2M. Cationic surface-active germicides and antibacterial compounds such as diisobutylphenoxyethoxyethyl dimethyl benzyl ammonium chloride, benzyl dimethyl stearyl ammonium chloride, tertiary amines having one fatty alkyl group (of from 12-18 carbon atoms) and two (poly) oxyethylene groups attached to the nitrogen (typically containing a total of from about 2 to 50 ethanoxy groups per molecule) and salts thereof with acids, and compounds of the structure

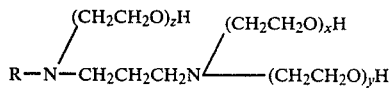

where R is a fatty alkyl group containing from about 12 to 18 carbon atoms, and x, y and z total 3 or higher, as well as salts thereof with mineral or organic acids, may also be used. It is preferred to use from about 0.05 to 5% by weight of the foregoing surface-active materials in the instant oral preparations.

Any suitable flavoring or sweetening materials may be employed on formulating a flavor for the preparation of the present invention. Examples of suitable flavoring constitutents include the flavoring oils, e.g., oils of spearmint, peppermint, wintergreen, sassafras, clove, sage, eucalyptus, marjoram, cinnamon, lemon and orange, as well as methylsilicylate. Suitable sweetening agents include sucrose, lactose, maltose, sorbitol, sodium cyclamate, perillartine and saccharine. Suitably, flavor and sweetening agents may together comprise from about 0.01 to 5% or more of the compositions of the instant invention. Chloroform may be used too.

Various other materials may be incorporated in the oral preparations of this invention. Examples thereof are coloring or whitening agents or dyestuffs, preservatives, anticorrosive agents, silicones, chlorophyll compounds, ammoniated materials such as urea, diammoniumphosphate and mixtures thereof and other constituents. Whitening agents, such as titanium dioxide, typically in amounts of about 0.5-2%, may be beneficial to the appearance of the dental preparation, since upon aging, preparations containing some polishing agents, e.g., sodium aluminosilicate and calcium carbonate undergo some discoloration.

The adjuvants are incorporated in the instant compositions in amounts which do not substantially adversely affect the properties and characteristics desired and are selected and used in proper amounts depending upon the particular type of preparation involved.

Antibacterial agents may also be employed in the oral preparations of the instant invention in an amount of about 0.01-5% by weight. Typical antibacterial agents include:

$N^1$-(4-chlorobenzyl)-$N^5$-(2,4-diclorobenzyl) biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-chlorophenylbiguanidohexane;
1,6-bis-(2-ethylhexylbiguanido)hexane;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
5-amino-1,3,bis(2-ethylhexyl)-5-methylhexahydro pyrimidine and their non-toxic acid addition salts.

Synthetic finely divided silicas such as those sold under the trademarks Cab-O-Sil M-5, Syloid 244, Syloid 266 and Aerosil D200 and mixtures thereof may also be employed in amounts of about 0.5-20% by weight to promote thickening or gelling of the dentifrice.

The following specific Examples are illustrative of the present invention. All amounts are by weight unless otherwise indicated.

EXAMPLES 1 TO 3

The following periodontal dental preparations are prepared and deaerated:

|  | 1 PARTS | 2 PARTS | 3 PARTS |
| --- | --- | --- | --- |
| Glycerine | 20.00 | 20.00 | 20.00 |
| Sorbitol (70%) | 43.62 | 43.38 | 42.80 |
| Sodium carboxymethyl cellulose | 0.21 | 0.21 | 0.21 |
| Sodium fluoride | — | 0.24 | — |
| Sodium monofluorophosphate | — | — | 0.82 |
| Sodium saccharine | 0.17 | 0.17 | 0.17 |
| Water | 3.00 | 3.00 | 3.00 |
| Sodium aluminosilicate (a silicate with a low combined alumina level) | 17.0 | 17.0 | 17.0 |
| Silica aerogel (Syloid 244) | 6.50 | 6.50 | 6.50 |
| Sodium lauryl sulphate (85%) | 2.00 | 2.00 | 2.00 |
| Folic acid | 0.50 | 0.50 | 0.50 |
| pH | 6.1 | 6.8 | 6.0 |

After aging for 3 months at room temperature and 43° C. the following retention levels of soluble folic acid are observed:

|  | % SOLUBLE FOLIC ACID RETENTION | |
| --- | --- | --- |
| PREPARATION | ROOM TEMPERATURE | 43° C. |
| 1 (Control) | 28.0 | 30.0 |
| 2 | 48.0 | 68.0 |

| PREPARATION | % SOLUBLE FOLIC ACID RETENTION | |
| --- | --- | --- |
| | ROOM TEMPERATURE | 43° C. |
| 3 | 104.0 | 96.0 |

Thus, compared with the control (1) more soluble folic acid is retained with sodium fluoride (2) present and essentially complete solubilization is observed when sodium monofluorophosphate (3) is present.

Grey discoloration occurs at room temperature and 43° C. in preparation 3 and at 43° C. for preparation 2. This can be reduced by adding additional 1% titanium dioxide to the preparations.

EXAMPLES 4 TO 6

The following periodontal dental preparations are prepared and deaerated:

| | 4 PARTS | 5 PARTS | 6 PARTS |
| --- | --- | --- | --- |
| Glycerine | 20.00 | 20.00 | 20.00 |
| Sodium carboxymethyl cellulose | 1.00 | 1.00 | 1.00 |
| Sodium fluoride | — | 0.24 | — |
| Sodium monofluorophosphate | — | — | 0.82 |
| Sodium saccharine | 0.17 | 0.17 | 0.17 |
| Water | 23.33 | 23.09 | 22.51 |
| Alpha-alumina trihydrate (British Aluminum AF 260) | 51.50 | 51.50 | 51.50 |
| Sodium lauryl sulphate (85%) | 2.00 | 2.00 | 2.00 |
| Folic Acid | 0.50 | 0.50 | 0.50 |
| pH | 6.0 | 8.0 | 6.2 |

After aging for 3 months at room temperature and 43° C. the following retention levels of soluble folic acid are observed:

| PREPARATION | % SOLUBLE FOLIC ACID RETENTION | |
| --- | --- | --- |
| | ROOM TEMPERATURE | 43° C. |
| 4 (Control) | 78.0 | 74.0 |
| 5 | 102.0 | 102.0 |
| 6 | 100.0 | 108.0 |

Thus, compared with the control (4) substantially greater essentially complete solubilization is observed when sodium fluoride (5) and sodium monofluorophosphate (6) are present.

Preparations 5 and 6 do not discolor; rather some not undersirable fading occurs at room temperature.

EXAMPLES 7 TO 9

The following periodontal dental preparations are prepared and deaerated:

| | 7 PARTS | 8 PARTS | 9 PARTS |
| --- | --- | --- | --- |
| Glycerine | 22.0 | 22.0 | 22.0 |
| Sodium carboxymethyl cellulose | 1.10 | 1.10 | 1.10 |
| Sodium fluoride | — | 0.24 | — |
| Sodium monofluorophosphate | — | — | 0.82 |
| Sodium saccharine | 0.2 | 0.2 | 0.2 |
| Water | 31.50 | 31.26 | 30.68 |
| Calcium carbonate | 42.00 | 42.00 | 42.00 |
| Sodium silicate (water-glass) | 0.2 | 0.2 | 0.2 |
| Sodium lauryl sulphate (100%) | 1.50 | 1.50 | 1.50 |
| Folic acid | 0.50 | 0.50 | 0.50 |
| pH | 7.7 | 9.0 | 7.9 |

After aging for 3 months at room temperature and 43° C. the following retention levels of soluble folic acid are observed:

| PREPARATION | % SOLUBLE FOLIC ACID RETENTION | |
| --- | --- | --- |
| | ROOM TEMPERATURE | 43° C. |
| 7 (Control) | 86.0 | — |
| 8 | 100.0 | 100.0 |
| 9 | 102.0 | 106.0 |

Thus compared with the control (7) essentially complete solubilization is observed when sodium fluoride (8) and sodium monofluorophosphate (9) are present.

Brown discoloration occurs at room temperature and 43° C. on preparation 9 and at 43° C. on preparation 8. This can be reduced by adding additional 1% titanium dioxide to the preparations.

EXAMPLES 10–12

The following periodontal dental preparations are prepared and deaerated:

| | 10 PARTS | 11 PARTS | 12 PARTS |
| --- | --- | --- | --- |
| Glycerine | 22.0 | 22.0 | 22.0 |
| Irish Moss | 1.40 | 1.40 | 1.40 |
| Sodium fluoride | — | 0.24 | — |
| Sodium monofluorophosphate | — | — | 0.82 |
| Sodium saccharine | 0.20 | 0.20 | 0.20 |
| Sodium benzoate | 0.15 | 0.15 | 0.15 |
| Water | 27.15 | 26.91 | 26.33 |
| Insoluble sodium metaphosphate | 45.60 | 45.60 | 45.60 |
| Titanium dioxide | 0.5 | 0.5 | 0.5 |
| Sodium lauryl sulphate (100%) | 1.50 | 1.50 | 1.50 |
| Folic acid | 0.50 | 0.50 | 0.50 |
| pH | 5.3 | 5.3 | 5.5 |

After aging for 3 months at room temperature and 43° C. the following retention levels of soluble folic acid are observed:

| PREPARATION | % SOLUBLE FOLIC ACID RETENTION | |
| --- | --- | --- |
| | ROOM TEMPERATURE | 43° C. |
| 10 (Control) | 44.0 | 46.0 |
| 11 | 94.0 | 50.0 |
| 12 | 54.0 | 40.0 |

Thus, compared with the control (10) greater soluble folic acid is retained with sodium fluoride (11) present (particularly upon aging at room temperature) and with sodium monofluorophosphate (12) at room temperature.

Upon aging at room temperature and 43° C. the colors of preparations 11 and 12 remain substantially unchanged.

We claim:

1. A periodontal dental preparation consisting essentially of about 0.01–5% by weight of folic acid, a dentally acceptable water-insoluble polishing agent which is principally sodium aluminosilicate, hydrated alumina, calcium carbonate, insoluble sodium metaphosphate, or a mixture thereof which polishing agent reduces the soluble folic acid present in the preparation and a fluorine-containing agent which increases retention of soluble folic acid in said preparation, the fluorine-containing agent being an alkali metal fluoride, an alkali metal monofluorophosphate, or a mixture thereof.

2. A periodontal dental preparation as claimed in claim 1 which is a dental cream or gel and has a pH of about 4–10.

3. A periodontal dental preparation as claimed in claim 1 wherein 10–75% by weight of the polishing agent is present.

4. A periodontal dental preparation as claimed in claim 1 wherein the fluorine-containing agent is present in amount which provides about 0.01–1% by weight fluorine.

5. A periodontal dental preparation as claimed in claim 4 wherein the fluorine-containing agent is sodium fluoride.

6. A periodontal dental preparation as claimed in claim 4 wherein the fluorine-containing agent is sodium monofluorophosphate.

7. A periodontal dental preparation as claimed in claim 1 wherein titanium dioxide is present.

* * * * *